(12) United States Patent
Davie

(10) Patent No.: US 9,924,653 B2
(45) Date of Patent: Mar. 27, 2018

(54) INCREASING THE NUMBER OF GRAIN BEARING EARS OF MAIZE

(71) Applicant: Kenneth Eric Jesse Davie, Harrismith (ZA)

(72) Inventor: Kenneth Eric Jesse Davie, Harrismith (ZA)

( * ) Notice: Subject to any disclaimer, the term of this patent is extended or adjusted under 35 U.S.C. 154(b) by 1154 days.

(21) Appl. No.: 14/017,598

(22) Filed: Sep. 4, 2013

(65) Prior Publication Data

US 2014/0013464 A1 Jan. 9, 2014

Related U.S. Application Data

(63) Continuation-in-part of application No. 11/597,305, filed as application No. PCT/ZA2005/000073 on May 23, 2005, now abandoned.

(30) Foreign Application Priority Data

May 21, 2004 (ZA) .................................. 2004/3951

(51) Int. Cl.
*A01H 5/10* (2006.01)
(52) U.S. Cl.
CPC ...................................... *A01H 5/10* (2013.01)
(58) Field of Classification Search
None
See application file for complete search history.

(56) References Cited

U.S. PATENT DOCUMENTS

| | | |
|---|---|---|
| 4,368,592 A | 1/1983 | Welch |
| 4,677,246 A | 6/1987 | Armond et al. |

OTHER PUBLICATIONS

Scott et al. (Crop Science, vol. 9, May-Jun. 1969, pp. 293-295).*
U.S. Appl. No. 11/597,305, filed Apr. 17, 2008, Davie, K.E.J.
Anderson, E.L., et al. 1984. Effect of N fertilization on silk synchrony, ear number, and growth of semiprolific maize genotypes. *Crop Science*. 24:663-666.
APPIN Investments CC Press Release. Breakthrough in maize breeding. Jan. 2005.
Bauman, L.F. 1959. Relative yields of first (apical) and second ears of semi-prolific southern corn hybrids. *Agronomy Journal*. 52:220-222.
Boyer, J.S. 1982. Plant productivity and environment. *Science*. 218(4571):443-448.
Boyle, M.G. et al. 1991. Stem infusion of liquid culture medium prevents reproductive failure of maize at low water potential. *Crop Science*. 31:1246-1252.
Casliglioni, V. et al. 1991. Effects of the introduction of the brachytic-2 gene in seven varieties of corn. *Revista Ceres*. 38(216):81-93. Viçosa/MG, Brazil.
Chaves, M.M. et al. 2002. How plants cope with water stress in the field. Photosynthesis and growth. *Annals of Botany*. 89:907-916.
Cheng, W.Y. et al. 2002. The vascular development in the na2/na2 mutant. Maize Genetics Cooperation Newsletter. 76:22-24.
Conger, B.V., et al. 1987. Somatic embryogenesis from cultured leaf segments of *Zea mays*. *Plant Cell Reports*. 6:345-347.
Cornic, G. 2000. Drought stress inhibits photosynthesis by decreasing stomatal aperture—not by affecting ATP synthesis. *Trends in Plant Sciences*. 5(5):187-188.
Davie, K.E.J. 1996. A more efficient maize plant. Abstracts of the Plant Breeding Symposium. Mar. 19-21. p. 22.
De Leon, N. and J.G. Coors. 2002. Twenty-four cycles of mass selection for prolificacy in the golden glow maize population. *Crop Science*. 42:325-333.
Dodd, J.L. 1980. Grain sink size and predisposition of *Zea mays* to stalk rot. *Phytopathology*. 70:534-535.
Dodd, J.L. 1977. A photosynthetic stress-translocation balance concept of stalk rot. American Seed Trade Association. Proceedings of the $32^{nd}$ annual corn sorghum research conference. pp. 122-130. Washington, D.C., United States.
Duncan, D.R. et al. 1985. The production of callus capable of plant regeneration from immature embryos of numerous *Zea mays* genotypes. *Planta*. 165:322-332.
Du Plessis, D.P., et al. 1967. The influence of the time lag between pollen- shedding and silking on the yield of maize. *S. Afr. J. Agric. Science*. 10:667-674.
Duvick, D.N. 1974. Continuous backcrossing to transfer prolificacy to a single-eared inbred line of maize. *Crop Science*. 14:69-71.
Earley, E.B. et al. 1974. Earshoot development of midwest dent corn. Illinois Experiment Station Bulletin, No. 747:2-44.
Fee, Rich. 1996. Production. *Successful Farming*. January p. 29.
Fee, Rich. 1996. Editor's Comment. *Successful Farming*. January pp. 54-55.
Flexas, J. et al. 2004. Understanding down-regulation of photosynthesis under water stress: future prospects and searching for physiological tools for irrigation management. *Ann. Appl. Biol*. 144:273-283.
Fournier, C. et al. 2000. Dynamics of the elongation of internodes in maize (*Zea mays* L.): Analysis of phases of elongation and their relationships to phytomer development. *Annals of Botany*. 86(3):551-563.
Ghannoum, O. 2009. C4 photosynthesis and water stress. *Annals of Botany*. 103:635-644.
Green, C.E. and Rhodes, C.A. 1982. Plant regeneration in tissue culture of maize. Plant Molecular Biology Association. Charlottesville, VA. pp. 367-372.
Grobbelaar, G. 2005. Dwarf maize variety holds big promise. Farmer's Weekly. Mar. 11. p. 23.

(Continued)

*Primary Examiner* — Brent Page
*Assistant Examiner* — Jared Shapiro
(74) *Attorney, Agent, or Firm* — Jondle & Associates, P.C.

(57) ABSTRACT

A maize plant and a method of increasing the number of grain bearing ears per plant is provided. The maize plants, irrespective of their variety, exhibit at least two adjacent shortened internodes (defined as being equal to or less than twice the largest transverse dimension of the stalk just above the ground) spacing at least two ear nodes. Preferably the internode spacing is about 70 mm or less. The maize plants are preferably selected such that the ears develop substantially synchronously; the silks start being exerted either at the same time as, or before, pollen is released by the tassels of the plants; and the maize plants are both of a dwarf maize type and a prolific plant type.

6 Claims, No Drawings

(56) References Cited

OTHER PUBLICATIONS

Hallauer, A.R. et al. 1972. Prolific corn hybrids and minimizing risk of stress. Proceedings of the 27th annual corn sorghum research conference. pp. 140-158.

Harris, R.E. et al., 1976. Control and inheritance of prolificacy in maize. *Crop Science*. 16(6):843-850.

Heichel, G.H. and Musgrave, R.B. 1969. Varietal differences in net photosynthesis of *Zea mays* L. *Crop Science*. vol. 9. July-August pp. 483-486.

Institute of Inventors and Innovators. 2004. Dwarf maize offers promise for seed market. Farmer's Weekly. Nov. 12. p. 81.

Jampatong, S. et al. 2000. Effect of one- and two-eared selection on stalk strength and other characters in maize. *Crop Science*. 40(3): 605-611.

Leng, E.R. and Ross, G.L. 1960. Performance of commercial hybrids in Illinois. Illinois Agr. Exp. Sta. Bul. 651:1-48.

Liddell, S. 2013. Crowding the field: Sustaining plant population growth the key to unlocking corn yield. Rabobank, Rabo AgFocus. January. pp. 1-8.

Loomis, R.S. and Williams, W.A. 1963. Maximum crop productivity: An estimate. *Crop Science*. 3:67-72.

Mock, J.J. and Pearce, R.B. 1975. An ideotype of maize. *Euphytica*. 24:613-623.

Mumm, W.J. 1958. Dwarf prolific corn. Maize Newsletter. 32:22-23.

Pendleton, J.W. and Seif, T.D. 1961. Plant population and row spacing with brachytic 2 dwarf corn. *Corn Crop Science*. 1:443-435.

Phinney, B.O. 1956. Growth response of single-gene dwarf mutants in maize to gibberellic acid. *PNAS*. 42(4):185-189.

Prine, G.M. 1971. A critical period for ear development in maize. *Crop Science*. 11:782-786.

Rao, K.V. 1986. Somatic embryogeneisis in glume callus cultures. Maize Genetics Cooperation Newsletter. 60:64-65.

Sanchez-Diaz, M.F. and Kramer, P.J. 1971. Behavior of corn and sorghum under water stress and during recovery. *Plant Physiol*. 48:613-616.

Sangoi, L. and R.J. Salvador. 1998. Maize susceptibility to drought at flowering: A new approach to overcome the problem. *Ciencia Rural*. 28(4):699-706.

Scott, G.E. and Campbell, C.M. 1969. Internode length in normal and brachytic-2 maize inbreds and single crosses. *Crop Science*. 9:293-295.

Siemer, F.G. et al. 1969. Timing and correlation of major developmental events in maize. *Agronomy Journal*. 61:14-17.

Songstad, D.D. et al. 1988. Effect of 1-aminocyclopropane-1-carboxylic acid, silver nitrate, and norbornadiene on plant regeneration from maize callus cultures. *Plant Cell Reports*. 7:262-265.

Sorrels, M.E. et al. 1979. Inheritance of prolificacy in maize. *Crop Science*. 19(3)301-306.

Tezara, W. et al. 1999. Water stress inhibits plant photosynthesis by decreasing coupling factor and ATP. *Nature*. 401:914-917.

Tollenaar, M. 1977. Sink-source relationships during reproductive development in maize: A review. *Maydica*. 22:49-75.

Torregroza, M. et al. 1989. Divergent mass selection for prolificacy in maize and its effect on the internode pattern. *Agronomia Colombiana*. 5:53-59.

Westgate, M.E. 1996. Physiology of flowering maize: identifying avenues to improve kernel set during drought. CIMMYT "Developing Drought and Low Tolerant Maize" Proceedings of a Symposium. Mar. 25-29. pp. 137-141. El Batan, Mexico.

Williams, W.A. et al. 1965. Vegetative growth of corn as affected by population density I. Productivity in relation to interception of solar radiation. *Crop Science*. 5:211-215.

Williams, W.A. et al. 1965. Vegetative growth of corn as affected by population density II. Components of growth, net at assimilation rate and leaf area index. *Crop Science*. 5:215-219.

Xu, N. et al. 2004. Co-regulation of ear growth and internode elongation in corn. *Plant Growth Regulation*. 44:231-241.

Poehlman, J.M., Breeding Field Crops, 1959, Henry Holt and Company, Inc., New York, 7 pages.

\* cited by examiner

INCREASING THE NUMBER OF GRAIN BEARING EARS OF MAIZE

CROSS REFERENCE TO RELATED APPLICATIONS

This application is a continuation-in-part of U.S. patent application Ser. No. 11/597,305 filed on Nov. 20, 2006, which is incorporated herein by reference in its entirety, which claims the benefit of the U.S. National Stage of International Application No. PCT/ZA2005/000073, filed on May 23, 2005 which was published in English as International Patent Publication No. WO 2005/112611 on Dec. 1, 2005, which claims priority to ZA2004/3951, filed on May 21, 2004. All references cited in this application are herein incorporated by reference.

FIELD OF THE INVENTION

The invention relates to increasing the number of grain bearing ears of maize and a method of developing modified maize plants with the aim of increasing grain yield capabilities.

BACKGROUND TO THE INVENTION

Maize is an important and valuable field crop. Thus, a continuing goal of plant breeders is to develop high yielding maize hybrids that are agronomically sound based on stable inbred lines. The reasons for this goal are obvious: to maximise the amount of grain produced with the inputs used and minimise susceptibility of the crop to environmental stresses. To accomplish that goal, the maize breeder must select and develop superior inbred parental lines for producing hybrids. This requires identification and selection of genetically unique individuals which in a segregated population occur as the result of a combination of crossover events plus the independent assortment of specific combinations of alleles at many gene loci which results in specific genotypes.

Several different strategies have been used to increase the grain yield of maize. The most generally utilised approach is to select for increased yield per se. Another approach is to try to preserve the inherent yield potential by reducing losses that occur due to disease and insect pests and following exposure to environmental stress. Thus, in many commercial programmes, breeders select for disease and insect resistance and tolerance of drought stress.

Another approach to increasing yields has been to increase the number of plants per unit area, typically per hectare or acre, or the "plant density". It has been stated that in the 1930s, maize farmers in the USA planted 10,000 plants per acre whereas by 1998, the farmers were planting 20,000 to 30,000 plants per acre. With increasing plant density maize plants tend to grow taller and become more susceptible to lodging. Thus, to develop commercial products adapted to higher planting rates, breeders have selected for resistance to stalk and root lodging.

Maize has shown a limited ability to increase yields of both dry matter and grain as plant densities are increased. Mock & Pearce (1975) described an optimum environment to produce maximum yields as including, among other factors, high plant densities and narrow rows. High plant densities and narrow rows permit increased leaf area index (LAI (Leaf Area Index)=leaf area per unit land area) allowing interception of more of the light energy reaching the earths surface.

Presently available maize plant morphologies (prolific phenotypes) often enable a maize plant to produce a second ear of harvestable grain but only if plant densities are below normal for typical growing conditions. Earley et al (1974) noted the yield of grain per plant was not limited by the lack of potential ears but by the failure of one or more of the earshoots to develop into sizeable ears. Results of experiments by Harris et al (1976) indicated that the certain lower earshoots abort because they reach the silking stage in poor synchrony with upper ear shoots. This was confirmed by studies by Sorrels et al (1979). As plant densities are increased, the incidence of plants with two ears becomes progressively lower. Prine (1971) concluded that under high plant densities competition for light during the critical silking period resulted in sizeable reductions in grain yield. Moreover, with increasing plant densities, the incidence of plants with multiple ears decreases more rapidly than the total vegetative matter per plant. Thus, obtaining a morphology which routinely produces multiple ears with harvestable grain, on a plant with equal or less total dry matter yield, would be an advantageous alternative for increasing yield. However, under very high plant densities, most of the plants are barren even though the total dry matter yield per unit area of land increases with increasing plant densities. Although grain yield is reduced at very high populations, the result is encouraging. This population response of the plant suggests that with appropriate technology to enable more efficient conversion of photosynthate into grain, the grain yielding potential of maize on a per acre basis could be further increased as well.

Attempts to improve the yield of maize by applying a dwarfing strategy used effectively in wheat and rice have not to date been successful. A widely used gene in maize is the brachytic 2 mutant. The lower internodes of brachytic 2 dwarfs are much shorter than in normal maize. Leng & Ross (1979) found that at comparable planting rates brachytic 2 dwarf hybrids showed better standability than their normal counterparts but yielded less. Subsequently, Pendelton & Sief (1961) found that the yield deficiency of brachytic 2 dwarfs could not be overcome by closer row spacings or higher plant populations. A more recent effort by Castiglioni et al (1991) studied the effects of the brachytic 2 gene following introduction into seven maize varieties. The introduction of the gene significantly reduced plant and ear height, plant lodging also decreased significantly. However, as with previous studies, grain yields declined compared to normal counterparts, and there was a measured reduction in the degree of prolificacy.

Research by plant physiologists has identified the magnitude of the supply of photosynthate available to convert into grain (also called "source" capacity), and the capacity to convert that supply into grain (also called "sink" capacity), as potentially limiting factors in maize yield. Tollenar (1977) summarised those reports by concluding that grain yield is limited by sink size in most temperate and subtropical maize growing environments, the exception being the northern areas of North America where the source appears to be limiting. The source limitations could be overcome by increasing LAI through high density plantings to the point when sink size ultimately becomes the limiting factor in grain yield, if not for the fact that eventually high plant density suppresses expression of prolificacy and reduces grain yield. Anderson et al (1984) conducting N rate studies confirm the results of Harris et al (1976) to the effect that reproductive sink size limits the yield of non-prolific hybrids. When sink size is the limiting factor, increasing the number of potential energy sinks (ear sites) could be achieved through improved multiple ear capability (prolificacy). Traditionally, Tollenar (1977) noted that increasing the amount of photosynthate to the ear during flowering would also increase yields. Thus, developing maize plants having improved multiple ear formation and increased available photosynthate during flowering would be desirable to improve the maize crop.

SUMMARY OF THE INVENTION

In accordance with one aspect of this invention there is provided a method of increasing the number of grain bearing ears per maize plant, the method comprising growing a maize type, wherein the maize type is selected such that at least the majority of the maize plants develop at least two adjacent shortened internodes spacing at least two ear nodes and a longer internode below the lowermost shortened internode provided that, in the event that the internodes are shortened down to ground level, such longer internode may be absent.

Further features of this aspect of the invention provide for the maize to be selected so that each maize plant develops two, three, four or more ear nodes that are spaced by an internode spacing sufficiently small, typically from about 1 mm to preferably not more than about 70 mm, to facilitate the development of more grain-bearing ears. Additional preferable attributes of the present invention include ensuring that the ears develop substantially synchronously; for the maize to be selected such that the silks develop either at the same time, or before, pollen is released by the tassels of the plants; for the maize to be selected such that the tassels are close to the silks; for the maize type to be a dwarf maize; for the maize to be a prolific plant type; and for the maize to be grown in high-density populations selected, with particular reference to maximising the use of available solar energy over the growing season.

In accordance with another aspect of the invention there is provided a maize plant that, irrespective of its variety, exhibits at least two adjacent shortened internodes spacing at least two ear nodes and a longer internode below the lowermost shortened internode provided that, in the event that the internodes are shortened down to ground level, such longer internode may be absent.

Another aspect of the invention provides for the maize plant to develop two, three, four or more grain-bearing ear nodes that are spaced by an internode spacing sufficiently small, typically from about 1 mm to preferably not more than 70 mm. For example, 1.0 mm, 5.8 mm, 10.2 mm, 14.7 mm, 19.2 mm, 22.0 mm, 28.5 mm, 33.0 mm, 46.8 mm, 54.7 mm, 62.9 mm, or 70.0 mm internodes lengths, including any integer or fraction thereof. In another aspect, maize plants of the present invention have ears that develop substantially synchronously. In another aspect of the present invention, the maize plants have silks that develop either at the same time as, or before, pollen is released by the tassels of the plants (protogyny). In another aspect, the maize plants of the present invention are dwarf maize types. In another aspect of the present invention, the maize plants are prolific plant types.

In one aspect, the maize morphology of the present invention includes at least two shortened internodes with each internode between grain-bearing ear nodes. The three or more ears developing from the ear nodes proximate to the shortened internodes develop relatively synchronously with each other. The shortened internodes of this maize phenotype are the result of one or more genetic loci. The internodes below the lowest grain bearing ear and above the apical ear, may be greater or lesser in length than those internodes between the grain-bearing ear nodes unless the internodes are shortened down to ground level.

The instant invention also encompasses the methods and processes of breeding or developing maize plants having at least two or more grain-bearing ears, shortened internode lengths, dwarf stature and silks that exert before or at the same time as pollen shed. Inbred lines, hybrids and any other maize plants with these traits are within the scope of this invention. Additionally, the present invention further encompasses regenerable plant materials therefrom and the processes by which plants may be regenerated from tissue culture and the tissue culture arising from regenerable tissues of maize plants of the present invention.

The instant invention also includes inbred lines to which the trait of this invention has been transferred either by conventional breeding strategies including but not limited to the pedigree breeding, breeding by doubling of haploids, recurrent selection breeding or backcrossing or by nonconventional biotechnology or genetic engineering strategies. Also included are hybrids made by crossing one or more inbred lines containing the trait of this invention.

A further embodiment of this invention is maize containing the trait of this invention, according to methods described from diverse germplasm sources containing the appropriate gene(s), and including for example, the maize lines designated APN301, APN303, APN304, APN305, APN318, APN342, APN343, APN344, APN345, APN347, APN501 and APN601. The maize lines designated APN301, APN303, APN304 and APN305 had a longer internode below the lowermost shortened internode, while the other lines had shortened internodes down to the ground-level.

A further feature of this invention is in the maize inbred or hybrids characterised by the trait of this invention.

Another aspect of the present invention provides a method for producing prolific, protogynous dwarf maize plants, the method comprising:
a) planting and growing a population of heterozygous maize plants;
b) selecting dwarf plants from said population to produce selected plants and inbreeding said selected plants to produce inbred plants;
c) planting and growing one or more prolific inbred maize plants and said inbred plants;
d) crossing said inbred plants with the prolific inbred maize plants to produce $F_1$ hybrid plants;
e) self-pollinating said $F_1$ hybrid plants to produce a segregating $F_2$ generation;
f) selecting prolific dwarf plants from said segregating $F_2$ generation;
g) self-pollinating the lowest ear of selected prolific dwarf plants; and
h) harvesting and growing seed from said lowest ear of selected prolific dwarf plants to produce self-pollinated prolific dwarf maize plants.

Another aspect of the present invention further comprises:
i) selecting protogynous plants from said self-pollinated prolific dwarf maize plants;
j) self-pollinating and growing selected protogynous plants until one or more prolific, protogynous dwarf maize plants are produced;
k) planting and growing seed of different maize plants and of said prolific, protogynous dwarf maize plants produced in step j);
l) bulking the pollen of the prolific, protogynous dwarf maize plants grown in step k) to produce bulked pollen;

m) pollinating the different maize plants grown in step k) with said bulked pollen to produce an $F_1$ population;
n) selecting vigorous plants from said $F_1$ population;
o) bulking the pollen of the selected vigorous plants to produce bulked pollen of the selected vigorous plants;
p) pollinating the selected vigorous plants with said bulked pollen of the selected vigorous plants;
q) selecting protogynous, dwarf plants having shortened internodes between the two top grain-bearing ears;
r) self-pollinating selected plants to produce seed of self-pollinated selected plants;
s) growing seed of self-pollinated selected plants;
t) repeating steps q) through s) until one or more inbred, protogynous, prolific dwarf plants are produced having internodes between the ears of about 70 mm or less.

Another aspect of the present invention provides for a method of producing prolific, protogynous dwarf maize plants, the method comprising:
a) growing a heterozygous population of two-eared maize plants;
b) selecting vigorous plants from said population;
c) bulking pollen from all of the selected vigorous plants to produce bulked pollen;
d) pollinating said selected vigorous plants with said bulked pollen;
e) harvesting and growing seed from the selected pollinated plants;
f) selecting plants having the shortest internodes between the top two ears;
g) self-pollinating selected plants having the shortest internodes for two or more generations, wherein in each generation protogynous, dwarf plants are selected having the shortest internodes between the top two ears; and
h) repeating steps e) through g) until prolific, protogynous dwarf plants are produced having shortened internodes between the ears of about 70 mm or less.

Another aspect of the present invention provides for a method of producing prolific, protogynous maize plants, the method comprising:
a) growing a heterozygous population of two-eared maize plants;
b) selecting protogynous plants;
c) bulking pollen collected from the selected protogynous plants and pollinating said selected protogynous plants with the bulked pollen;
d) harvesting seed from said pollinated selected plants;
e) growing said harvested seed;
f) selecting protogynous maize plants; and
g) repeating steps b) through f) until prolific, protogynous maize plants are produced.

Another aspect of the present invention further comprises:
h) crossing said protogynous, prolific plants produced in step g) with a dwarf maize plant using the tandem backcross breeding method to produce progeny plants; and
i) inbreeding said progeny plants and selecting for prolific, protogynous, dwarf plants having shortened internodes between the ears of about 70 mm or less.

In another aspect of the present invention, selected vigorous plants have well-developed tillers. A further aspect of the present invention provides for inbred and hybrid plants produced by the method of the present invention.

DETAILED DESCRIPTION OF THE INVENTION

In the description and tables that follow, a number of terms are used. In order to provide a clear and consistent understanding of the specification and claims, including the scope to be given such terms, the following definitions are provided:

Acropetally. Development of organs in succession towards the apex, the oldest at the base, the youngest at the tip, for example the leaves on a shoot.

Assimilate. The product of photosynthesis used by a plant to produce grain.

Basipetal. The development of organs in succession towards the base, the oldest at the apex, the youngest at the base.

Canopy. The state at which the plants cover the whole area and intercept virtually all the light.

Drought. A period of dry weather, especially a long period of dry weather that is injurious to crops.

Dwarf maize plant. As used herein, 'dwarf' maize plant refers to a maize plant with a height of 150 centimeters or less, preferably with a height of 120 cm or less.

Ear node. A node at which an ear develops.

FIL. Floral internode length

F1. First generation cross.

F2. Second generation from a self pollinated cross.

F3. Third generation from a cross which results from the self pollination of the F2, and so on.

Grain bearing ear. A maize ear having at least 1 kernel.

Heterozygous. Having the two alleles at corresponding loci on homologous chromosomes different for one or more loci.

Heterozygous maize plant or plants. As used herein, refers to a maize plant or plants that are heterozygous at one or more loci. Examples include, but are not limited to, an open-pollinated variety or landrace.

High density population. As used herein, refers to maize plants planted at a density of over 90,000 plants per hectare.

Homozygous. As used herein, means that the pairs of chromosomes of a plant have identical genes at corresponding gene loci.

Ht. A gene for resistance to maize leaf blight.

HtN. A gene for resistance to northern maize leaf blight.

Inbred line. As used herein, refers to individuals of a particular species which are nearly identical to each other in genotype due to inbreeding.

Inbreeding. As used herein, refers to self-pollination of successive generations of plants descended from a single original plant, in order to achieve homozygosity.

Internode. The part of the plant stem between the two successive nodes.

Internode spacing. The distance between nodes.

Kernel. A viable maize seed that can be grown to produce a maize plant.

KSM. Refers to a composite of selections of maize streak virus resistant selections of the K64 inbred line into which the streak virus resistance genes had been introgressed. K64 is an inbred developed in Kentucky.

LAI. Leaf Area Index. The area of leaf per unit area.

Landrace. As used herein, landraces are highly diverse populations and mixtures of genotypes grown by subsistence farmers.

Lodging. The falling over of plants.

MEWI. Multiple Ear grain Weight Index.

Morphology. Form and structure of a maize plant.

Node. Part of the plant stem where one or more leaves or ears arise.

Phenology. The study of periodic phenomena of plants, for example, the time of flowering in relation to climate.

Photosynthate. A biochemical product of photosynthesis.

Photosynthesis. The process by which green plants, algae, diatoms, and certain forms of bacteria make carbohydrates from carbon dioxide and water in the presence of chlorophyll, using energy captured from sunlight by chlorophyll, and releasing excess oxygen as a byproduct. In plants and algae, photosynthesis takes place in organelles called chloroplasts. Maize has a modified photosynthetic pathway that allows it to survive extended periods of drought.

Pollen shed. Refers to the release of pollen from the anthers on the tassel.

Pollination. The transfer of pollen from the anther to the stigma.

Polygene. A group of genes that together influence a phenotypic trait. Polygenic inheritance occurs when one characteristic is controlled by the additive effects of each of two or more genes, with each contributing gene having small and relatively equal effects, and can be measured quantitatively, such as plant height.

Population. As used herein, refers to a mixture of maize plants and/or seeds of various genotypes.

POWS. An opaque-2 two-eared synthetic maize population produced out of the Natal Potch Pearl variety.

Prolific plant. Refers to a maize plant having at least two or more grain bearing ears.

Prolificacy. The ability of the maize plants to produce at least two or more grain bearing ears.

Protogyny. As used herein, protogyny refers to the female flower (the ear in maize) exerting silks at the same time or before the male flower (the tassel) sheds pollen.

Shank. The portion of the lateral branch below the ear.

Shortened (or short) Internode. As used herein, shortened internode refers to internode lengths of less than about 70 mm. For example, 1.0 mm, 5.8 mm, 10.2 mm, 15.7 mm, 19.2 mm, 22.6 mm, 27.5 mm, 33.0 mm, 38.7 mm, 46.8 mm, 54.7 mm, 62.9 mm, or 70.0 mm internodes lengths, and including any integer or fraction thereof.

Silk. The stigma and style of the female part of the maize.

Silking. The emergence of the silks from the ear.

Sink. The ability of the grain to accommodate or use the assimilate (photosynthate).

Source. Supply to the grain of the products of photosynthesis (assimilate or photosynthate).

Substantially synchronously. The silks emerge starting with those at the base (proximal end) of the ear and progress towards the tip (distal end) of the ear. As a result, the silks of any one ear take about three days for all the silks to be exerted. Ears whose silks are exerted within about three days of the first ear starting to exert its silks, exert part of their silks synchronously with the first ear and with each other.

Tandem backcross breeding method. As used herein, refers to a method of successively backcrossing plants to the recurrent parents that is used for transferring a large number of recessive genes to progeny, as shown in Table 3.

Tassel. The terminal male inflorescence of some plants and especially maize.

Tillers. Vegetative or reproductive shoots that grow from the axillary buds at the lower stalk nodes of a maize plant. Commonly referred to as 'suckers'. 'Well-developed tillers' are tillers that are about half to three quarters the height of the mother plant.

Vigorous plant. As used herein, a vigorous plant means a strongly growing healthy plant.

As a result of more efficient photosynthesis, there is a higher level of photosynthates (assimilate, sugars) at all stages of development. At low plant density a larger area of the leaves of each plant is exposed to sunlight than at high plant densities; more photosynthetically efficient plants then produce sufficient sugars to enable a larger number of ear buds to develop and produce grain, whereas less photosynthetically efficient plants continue to produce only one or two ears. At very high plant densities, maize plants shade each other, which significantly reduces the area of leaf of each plant that is exposed to light; less photosynthetically efficient plants as a result fail to produce enough sugars to produce grain, i.e., they are barren. At very high plant densities, only the plants that are the most efficient photosynthetically are able to produce enough sugars to produce grain. In a drought during flowering of maize, higher sugar levels in plants enable the kernels to continue developing, while at lower sugar levels the kernels abort in a drought. Further, at flowering, the higher level of photosynthate has as a consequence that the level of photosynthate required for the silks to be exerted is reached earlier than three days after anthesis and even before anthesis (protogyny).

The method of breeding maize provided by the present invention makes it possible to increase the number of grain-bearing ears that individual plants produce, that is, to increase the sink capacity of the maize plant. This is achieved by the selection of protogynous plants in a segregating population and at the same time by selecting for very short internodes between the ears. The short internodes appear to lower the threshold at which the nodes at either end of the internodes are stimulated to produce ears. Selecting for short internodes between the top two ears can lead to the other internodes of the plant becoming short as well. In one embodiment, if the internodes are shortened down to ground level this can lead to multiple ears being stimulated to develop down to the node below ground level provided that the plant has the photosynthetic capacity (source) to fill them and no other limiting factor (usually environmental) starts to limit the supply of photosynthate.

The plants that are able to produce grain bearing ears down to the node below ground level at relatively low population densities are highly desirable because they are very short and have a very high photosynthetic capacity. These indicate a strong potential and suitability to produce grain on at least the top ear at extremely high population densities. The ears will produce grain provided that the plant has the photosynthetic capacity to fill them. In this way grain bearing ears can continue to be added up to the limit of the plant's photosynthetic capacity (source) or until some other limiting factor, usually environmental, starts to limit the production of photosynthate in the maize plant.

The impact of short internodes on ear formation is unique and in contrast to a number of findings of other researchers. Torregroza et al (1988) looked at the impact that breeding for prolificacy had on internode pattern and found that prolific populations had more and longer internodes than non-prolific populations. They also noted that the increase in internodes number occurred below the ear increasing both ear height and plant height which is not advantageous in a commercial product. Sorrells et al (1979), in studying the inheritance of prolificacy, noted that there were a few correlations observed between internode lengths and either ear number or MEWI (an index of multiple ear grain weight).

Photosynthesis is slowed down or stopped when plants are stressed, such as from drought or high-density populations. When maize plants are drought stressed during flowering and pollination, the silks are withheld and pollination is inhibited; however, when the plants receive moisture and the plants are no longer stressed, the silks emerge. Silks therefore require a certain level of photosynthate in order to emerge.

Due to the increased photosynthetic efficiency of the protogynous short internode dwarf plants, there is an increased production of photosynthate. The increased level of photosynthate (sugars) stimulates the silks to emerge earlier in relation to pollen shed (protogyny) and stimulates the production of multiple ears (prolificacy). It also enables the plants to continue producing ears at very high population densities (at least 90,000 plants per hectare without irrigation). The degree of protogyny can be modified by competition for photosynthate by the ears. For example, the inbred APN601 of the present invention has five ears, and three of which have silks that start to emerge at the same time as pollen shed commences. It appears that none of the ears have silks that start to emerge before pollen shed commences because of the amount of photosynthate required for the production of the five ears.

A critical characteristic of the present invention is the reduction of internode length between the nodes which develop ear shoots or buds (ie ear nodes). When the internode length is reduced to below a certain critical distance (i.e., less than 70 mm), the proximal ears develop synchronously as if the control system of the plant treated these multiple ear nodes as a single unit. Thus, if each of the internodes between the top three or four ear nodes is less than a certain critical distance, the ear shoot primordia adjacent to these ear nodes will develop simultaneously. Moreover, if the internode lengths are shortened to between less than about 1 mm and less than about 70 mm then the proximal developing ears may have virtually equal access to the available photosynthate. Regardless of the mechanism of the present invention, up to seven or eight ears may develop on plants, whereas otherwise only the top one or two shoots would develop. In addition, the development of these ears is more synchronised. If the supply of photosynthate is adequate, all of the ear shoots will fill and produce grain at relatively low population densities.

The critical internode length can be somewhat affected by the vigor or overall height of the plant. The critical internode length required for a plant whose vigor has been reduced by inbreeding is less than 70 mm, and preferably about 50 mm or less, while the critical internode length for a vigorous and taller hybrid resulting from the cross of two such inbred plants may be greater than 70 mm.

Another desirable feature of the present invention is for the maize plant to have the capability to silk before the onset of pollen shed. Extended delay of silking can cause silking to occur at a time when the amount of viable pollen is either greatly reduced or no longer present. In such cases, few or no kernels are formed on these ears and grain yield is severely reduced. Plants having silks which normally begin to emerge a few days before pollen shed are more resistant to both drought and higher population densities compared to plants which silk after the onset of pollen shed. During times of stress, the silks of these early silking plants are delayed, however, silk emergence is still more fully synchronised with pollen shed. Therefore even during times of stress there is sufficient viable pollen to effect fertilisation. Hence, ears with full compliments of grain are enabled.

One feature of the present invention is that dwarfing results in a smaller plant having less tissue. Thus, less energy is required to grow and sustain the reduced amount of tissue for a smaller plant versus larger plants. These lower energy requirements should enable more photosynthate to be used for grain production. Moreover, a shorter stalk indicates the total volume of the plant is smaller than otherwise. As population density increases, individual plants are more and more shaded by neighboring plants. This means that as population density increases, a smaller and smaller area of leaf of each of the individual plants is exposed to sunlight. It follows that those plants that are the most photosynthetically efficient are able to continue producing sufficient photosynthate with a smaller area of leaf that is exposed to sunlight in order to continue producing grain-filled ears. Therefore, another advantage of the smaller plant volume is the resulting higher concentrations of photosynthate expected during the critical flowering period. The higher concentrations of photosynthate would promote the development of a number of potential ear shoots that can develop into mature ears bearing harvestable grain. The dwarfing mechanism of the present invention is distinct from and does not have the shortcomings previously referenced regarding the use of brachytic 2 dwarf gene, such as decreased grain yield and reduction in the degree of prolificacy.

As population density increases, mutual shading results in a reduction in the amount of solar radiation received by individual plants. Less solar radiation means less photosynthesis and thus lower grain production by individual plants. Grain production is reduced from the lowest ear upwards. As population density increases a point is reached where only one ear, the top ear, produces grain. At even higher population density no grain at all is produced. Even though the individual plants produce less grain where one ear per plant sets grain, the yield per unit area is greater because of the greatly increased number of plants per unit area. All things being equal, the most efficient plants, namely those that produce the most ears and therefore grain at lower population densities, can be expected to produce at least one ear per plant at the highest population densities where less efficient plants produce no ears at all.

It is known that plants with one or more fully developed ears are more susceptible to lodging than plants without developed ears. It is generally believed that increased competition between developing ears and the stalk for photosynthate causes greater reallocation of stalk carbohydrates to the grain sink. This may predispose the plant to root senescence followed by root rot and stalk rot, Dodd (1977) and Duvick (1974). It is also known that taller plants and plants with greater ear heights are more susceptible to lodging because of the physical leverage of the wind during storms in comparison to shorter plants and plants with lower ear heights. Thus, the very short stalk length above the ear and the decreased ear heights and often thicker stalks of dwarf selections of the maize plants of the present invention are less prone to lodging than the current morphologies in commercial use for stalks of equal strength. Therefore another desirable, but not essential feature of the improved maize morphology of the present invention, is that it includes a lower ear height and a lower susceptibility to lodging, for stalks of equal strength, than the current commercial maize morphologies.

To ensure the greatest possible amount of photosynthetic activity, the leaves should be upright in such a way as to allow for efficient light penetration into the leaf canopy. Mock & Pearce (1975) indicated leaf orientation (ie angle of the leaf blades relative to the stem) to be of prime importance with respect to light interception by plants grown at high plant densities. It is especially advantageous, but not essential to the improved maize morphology of the present invention that the orientation of the upper leaves be upright so that as much sunlight as possible penetrates to the photosynthetic tissues proximate to the developing ears. Long broad lower leaves would also be beneficial but not essential to the present invention in that they would increase leaf area and enable the plants to canopy earlier and so increase productivity.

A consistent impediment to determining the mechanism of drought-induced loss of crop productivity has been the inability to experimentally separate the effects of low assimilate supply (photosynthate) from the effects of low water availability. However, Boyle et al., 1991, succeeded in demonstrating that assimilate supply and not low water availability per se was the limiting factor in maize reproductive failure near anthesis. It appears that higher photosynthetic efficiency improves the assimilate supply during drought stress.

Another important feature of the present invention is tolerance to higher populations. In a study of the maize industry in the U.S. by Rabo Bank, it was concluded that 80 percent in yield increase in U.S. maize depends on increased population density rather than generating more maize per plant. It is well established in the art of maize production that hybrids of prolific tendencies respond more favourably to high-density planting than single eared plant types. Data from Bauman (1959) confirmed the ability of prolific hybrids to resist barrenness at high plant densities or under other stress environments. Normal single-eared hybrids only adjust to higher plant densities, in addition to increased barrenness, by reduction in ear size. In contrast, prolific hybrids adjust to higher densities only by reduction in ear number with no barrenness and relatively constant ear size. This was confirmed by Hallauer & Troyer (1972). Thus, the maize morphologies of the present invention which are able to produce three or more grain bearing ears per plant, and higher plant densities, confer even greater yield responses. Other beneficial but non essential attributes of the present invention are a high resistance to disease and a large fibrous root system with a large number of hair roots which means that the surface area in contact with the soil is much larger than a plant which has a smaller root system and few hair roots. This could be important under low moisture conditions as a larger surface area increases the ability of the plant to extract moisture from the soil.

Another advantageous, but not essential feature of the present invention is an improved maize morphology via a reduction in tassel mass. Mock & Pearce (1975) included tassel size as an important trait of their maize ideotype. They suggested that small tassels should reduce both the shading of the upper leaf layers and the ability of the tassel to compete with the ears for assimilate. Smaller tassels would reduce the photosynthate required for pollen growth and development and thus free more photosynthate for grain production. Moreover, less shading of the underlying canopy also occurs, thereby further increasing the photosynthetic potential of leaves proximate to the developing earshoots.

EXAMPLES

Example 1. Enhancing the Production of Maize—Breeding with 136Dw

The present invention emerged from a maize breeding program initiated to increase the productivity of the crop. The first step was to select for a dwarf plant type in combination with selection for tillering and prolificacy. A dwarf plant was selected in a Zulu landrace and was then inbred to produce the line 85-W-Dw in 1981. Another dwarf plant was selected in the Mostert open pollinated variety and was also inbred to produce the line 84-14. Both the Mostert variety and the Zulu landrace were heterozygous. In order to select polygenic dwarf plants it is essential and preferable to do so in heterozygous populations such as landraces and open pollinated varieties where plant height genes are usually segregating and there is an increased probability of finding polygenic dwarf plants. Inbred lines 85-W-Dw and 84-14 were both polygenic dwarf lines. The 85-W-Dw line had single ears and 84-14 formed tillers. The $F_1$ hybrid between these inbreds was also a dwarf, but the yield was poor.

To increase the vigor and strengthen the heterotic response, in 1983 the 85-W-Dw inbred was crossed to B254W, a prolific two-eared inbred line, and the resulting $F_1$ hybrids were self pollinated using a method of the present invention. Among the segregating $F_2$ progeny, dwarf plants with at least two well developed ear shoots were selected and further inbred. Among the progeny of the cross were some plants which produced two well-developed ear shoots, but tended to produce grain on the top ear only. By pollinating the lowest ear only, several dwarf prolific inbred lines were bred which exerted their silks before pollen shed (protogyny). These lines were designated 136W.Dw. Protogyny was regarded as beneficial and thereafter protogynous plants were favored when selecting.

In order to produce more prolific dwarf inbred lines, inbred lines such as A228N, $B73^6$.Ht.HtN and A554N (as derivative of $M37W^3$.O2FL2) were pollinated with bulked pollen of the 136W.Dw lines. $B73^6$.Ht.HtN and A228N are single-eared inbreds. In 1989, the cross A228N×136Dw lines bulk was tall and had a high proportion of tillering plants, which were pollinated with bulked pollen from all the tillering plants. In the segregating progeny of [(A228N× 136Dw lines bulk) Tillering×Tillering bulk] short protogynous prolific plants were selected and self-pollinated. At the same time plants with the shortest internodes between the two ears were selected. In the second generation, a sudden decrease in internode length was found in one plant namely, [(A228N×136Dw lines bulk) Tillering×Tillering bulk]-9-8, which was protogynous and had two seed-bearing ears with an internode 30 mm long between them. The internode between the second and third ear was 70 mm long; however, the third ear shoot did not set seed.

Unexpectedly, the progeny of [(A228N×136Dw lines bulk) Tillering×Tillering bulk]-9-8 were highly prolific. Selection 6 had four well developed ears, but seed set was poor. The next year, the fertilizer level was increased and led to a great improvement in seed set in the multiple-eared plants. The great increase in the number of ears in the protogynous plants followed the great reduction in the internode length between the top and the second ears. Selecting for a shorter internode length between these two ears also led to a reduction in the length of the internodes above and below it. Internodes of less than about 70 mm appeared to be necessary for increased prolificacy, and with continued self-pollinations of inbred line [(A228N×136Dw lines bulk) Tillering×Tillering bulk]-9-8, several protogynous inbred lines were produced characterised by dwarf stature and prolific plant type with short internodes between the ears that silk synchronously. The lines APN301, APN303 and APN305 exemplify this plant type and are part of the present invention.

Line development continued on a number of materials. Unexpectedly, the greatest success was obtained where pollinations were made with bulked pollen. This allowed for a large number of combinations of genes to take place. For example, the single-eared inbred line $B73^6$.Ht.HtN was pollinated with bulked pollen of the 136W.Dw lines in 1989, which after further crossing and selection as described produced inbred lines APN318, APN342, APN343, APN344, APN345, APN346 and APN347 of the present invention, which are characterised by dwarf stature and prolific and protogynous plant type with short internodes between ears that silk simultaneously.

Table 1 shows the height, internode lengths, number of grain bearing ears and number of protogynous ears of a number of dwarf inbred maize lines created by the breeding methodology set forth in Example 1, as compared to their initial inbred parent, A228N or B73[6].Ht.HtN. Column 1 shows the inbred name, column 2 shows the plant height in cm, column 3 shows the internode length in mm below the top ear, column 4 shows the internode length in mm between the second and third ears, column 5 shows the internode length in mm between the third and fourth ears, column 6 shows the number of ears per plant, and column 7 shows the number of protogynous ears. An asterisk indicates data not available.

TABLE 1

| Inbred | Height (cm) | Internode below top ear (mm) | Internode 2$^{nd}$ & 3$^{rd}$ ears (mm) | Internode 3$^{rd}$ & 4$^{th}$ ears (mm) | Number of ears | Number of protogynous ears |
|---|---|---|---|---|---|---|
| A228N | * | * | — | — | 1 | 0 |
| APN301 | 98 | 25 | 25 | 35 | 3-4 | 2-3 |
| APN303 | 101 | 45 | 50 | — | 3-4 | 2-3 |
| APN305 | 103 | 23 | 46 | — | 3-4 | 2-3 |
| B73[6] | 181 | 109 | — | — | 1 | 0 |
| APN318 | 51.5 | 24 | 35 | — | 3-4 | 3 |
| APN342 | 97 | 46 | 39 | — | 3 | 2 |
| APN343 | 88.5 | 34 | 45 | — | 3 | 2 |
| APN344 | 84.4 | 40 | 41 | — | 3 | 2 |
| APN345 | 81.2 | 36 | 29 | — | 2 | 2 |
| APN346 | 90 | 66 | 66 | — | 3 | 2 |
| APN347 | 72.5 | 61 | 60 | — | 3 | 2 |

As shown in Table 1, inbred protogynous, prolific dwarf maize produced by the method of the present invention have shorter height, shorter internode lengths and greater number of ears and protogynous ears than the inbred parental lines A228N and B736.Ht.HtN.

Table 2 compares the number of grain bearing ears per plant of the instant invention, dwarf inbred varieties APN303 and APN318, to that of Bushman, an open pollinated variety, and PHB 33D99, a commercial hybrid.

TABLE 2

| No. of Ears per Plant | APN303 | APN318 | Bushman | PHB33D99 |
|---|---|---|---|---|
| 0 | 0 | 0 | 1 | 1 |
| 1 | 0 | 0 | 12 | 10 |
| 2 | 1 | 1 | 9 | 12 |
| 3 | 18 | 17 | 1 | 0 |
| 4 | 4 | 5 | 0 | 0 |
| Total plants | 23 | 23 | 23 | 23 |
| Total ears | 72 | 73 | 33 | 34 |
| Average ears/plant | 3.13 | 3.17 | 1.43 | 1.48 |

As shown in Table 2, plants of the instant invention, APN303 and APN318, unexpectedly have significantly more plants bearing 3 or 4 ears of maize than PHB33D99 and Bushman. It follows that plants of the instant invention are more prolific than the reference plants.

Example 2. Enhancing the Production of Maize—Breeding with KSM

KSM, a maize streak virus resistant composite, was obtained from the Grain Research Institute in Potchefstroom, South Africa. KSM was completely unrelated to the A228N and B254W starting material described in Example 1. In summer of 1990/1991, out of a population of the KSM plants, vigorous plants with tall tillers were selected and pollen from the selected plants was bulked. The bulked pollen was used to pollinate the selected plants, the seed produced was harvested and grown, and plants were selected having the shortest internodes between the top two ears. By self-pollinating and selecting for protogyny, dwarf plants, and short internodes between the top two ears in each generation, a dwarf plant was selected and designated (237-906×tillering sib)-58D-3-11-6-23-4, which had two ears that produced silks prior to commencement of pollen shed, had a height of 990 mm and had internodes lengths measuring 22 mm and 30 mm between the three ears in the fifth generation of inbreeding. This protogynous dwarf plant was further used to breed lines from 124$^2$.195, which was M162W, an inbred line obtained from the Summer Grain Center in Pietermaritzburg that had been converted to dwarf. A fourth generation inbred selection in one of these lines, designated 48R was 855 mm tall, was protogynous and had four ears. The internodes between the ears measured 75 mm, 60 mm and 20 mm from the top ear downwards.

Example 3. Enhancing the Production of Maize—Breeding with POWS

POWS, an opaque-2 two-eared synthetic population was produced out of the Natal Potch Pearl variety (designated NPP Opaque-2) by Dr. H. O. Gevers of the Summer Grain Center in Pietermaritzburg, South Africa. In 2000, POWS was planted at low population density along the border of the breeding nursery. Plants with a few silks just starting to emerge before pollen shed commenced were marked, and bulked pollen from all the marked plants was used to pollinate the marked plants. Pollinating with bulked pollen of selected plants made it possible to accumulate desirable genes into individual plants. In the case of self-pollination, the progeny are restricted to the genes that occurred in the parent and many of the progeny have fewer desirable genes than the parents due to gene segregation. With each generation of bulk pollination, plants were selected that were more and more protogynous. After the second cycle of pollinating plants with bulked pollen of protogynous selections, a plant that exerted its silks four days before the commencement of pollen shed was self-pollinated. One of its progeny, designated 41e, had seven ear shoots that exerted their silks before pollen shed commenced. All seven ears of 41e set seed; however, the plant was tall and the lengths of the internodes between the ears varied from 105 mm to 140 mm. Previous to this event it had seemed that short internodes between the ears caused prolificacy. This event, together with the result obtained in Example 1 indicated that protogyny was probably the most important factor in increasing the number of grain-bearing ears and that short internodes reduce the threshold at which an increased number of grain-bearing ears are stimulated to develop.

To produce multiple-eared dwarf plants from 41e, crosses were made with a prolific dwarf 868D using the tandem backcross breeding method as described in Table 3. An inbred designated APN501 was selected in the seventh generation of inbreeding and produced four ears with internode lengths of 16 mm, 21 mm and 32 mm. The first, second and fourth ears of APN501 started exerting their silks three, two and one days before the onset of pollen shed, respectively. Table 4 below shows a comparison of characteristics of inbred APN501 of the present invention versus the original opaque-2, two-eared synthetic, designated NPP Opaque-2. Table 4, column 1 shows the inbred, column 2 shows the height in centimeters (cm), column 3 shows the internode lengths below the top ear in mm, column 4 shows the internode lengths between the $2^{nd}$ and $3^{rd}$ ears in mm, column 5 shows the internode lengths between the $3^{rd}$ and $4^{th}$ ears in mm, column 6 shows the number of ears, and column 7 shows the number of protogynous ears.

TABLE 3

| Generation | Crosses | | | Generation |
|---|---|---|---|---|
| F1 | A (prolific dwarf) × B (conventional maize) | | | F1 |
| | ↓ | | | |
| | (50% A genes) | A · B | (50% B genes) | |
| Backcross 1 to A | A · B × A | | A · B × B | Backcross 1 to B |
| | ↓ | | ↓ | |
| | $A^1$ · B (25% B genes) | | A · $B^1$ (25% A genes) | |
| Tandem backcross 1 | $A^1$ · B × A · $B^1$ | | A · $B^1$ × B | Backcross 2 to B |
| | ↓ | | ↓ | |
| | A1 · $B^{TBC1}$ (50% B genes) | | A · $B^2$ (12.5% A genes) | |
| Tandem backcross 2 | $A^1$ · $B^{TBC1}$ × A · $B^2$ | | A · $B^2$ × B | Backcross 3 to B |
| | ↓ | | ↓ | |
| | A1 · $B^{TBC2}$ (68.75% B genes) | | A · $B^3$ (6.25% A genes) | |

TABLE 4

| Inbred | Height (cm) | Internode below top ear (mm) | Internode $2^{nd}$ & $3^{rd}$ ears (mm) | Internode $3^{rd}$ & $4^{th}$ ears (mm) | Number of ears | Number of protogynous ears |
|---|---|---|---|---|---|---|
| NPP Opaque-2 | 175 | 137 | — | — | 2 | 0 |
| APN501 | 102.2 | 16 | 21 | 32 | 4 | 3 |

As shown in Table 4, inbred APN501 produced by the method of the present invention unexpectedly has a dwarf stature with shortened internodes and an increased number of ears and increased protogynous ears, when compared to the original parent plant.

Example 4. Enhancing the Production of Maize—Standardizing Height Genes to Produce Dwarf Hybrids A most important objective of the present invention is to produce prolific dwarf hybrid maize. Because there are many polygenes in maize, dwarf plants derived independently of each other do not necessarily have the same dwarf genes. The result is that when different dwarf lines are crossed they do not necessarily produce dwarf hybrids. Therefore, it is essential to have a method of standardizing height genes in order to produce dwarf hybrids when dwarf inbred lines are crossed. Two crosses were made: 1) inbred line Mo17$^8$.Ht,HtN (Mo17) was crossed to a Mostert dwarf line and, 2) a (A228N×136.Dw lines bulk) selection was backcrossed twice to Mo17. Resulting selections from the two crosses were crossed with each other and produced dwarf inbreds; however, when the dwarf inbreds were crossed to inbred APN318 of the present invention, they did not result in dwarf hybrids. To remedy this, a dwarf inbred produced from the two crosses was crossed to APN318 and then backcrossed to the Mo17 derivative. The backcross was self-pollinated to give a segregating population and protogynous dwarf prolific plants with short internodes were selected. The selections were self-pollinated and test crosses with each one of them were also made onto APN318. The seed of the self-pollinated selections and the test crosses were planted and the selections whose test crosses were tall were discarded. Those whose test crosses were dwarf height were self-pollinated. The selections continued to be inbred while selecting for protogyny, prolificacy and short internodes. Seven generations of inbreeding resulted in inbred line APN601 of the present invention. APN601 when crossed to APN318 results in dwarf hybrid plants. APN601 is 815 mm tall with internode lengths of 8 mm, 15 mm, 21 mm and 6 mm between the top and second ear, second and third ears, third and fourth ears, and fourth and fifth ears, respectively. Surprisingly, APN601 has 5 ears, with 3 ears starting to silk in synchrony with the start of pollen shed. Conversely, Mo17 is 1870 mm tall with an internode length of 145 mm below the top ear and has 1 ear.

Example 5. Comparison of Maize Hybrids Derived from A554N and Mo17

In the 2000/2001 growing season, a trial was planted comparing the hybrid A554N×Mo17$^8$.Ht,HtN with early test crosses of the derivatives of the two parent lines of the hybrid to which short internodes and protogyny had been added. The population density of the trial was 38,500 plants per hectare, which is the density at which farmers in the area plant dry land (rain fed) maize because of the risk of drought. The intention of the trial was to determine whether the addition of short internodes and protogyny would increase the yield of the hybrid. The derivatives used in the comparison were derivatives of inbred A554N, including 460D (self 3), 462D-9 (self 4), 591D (self 4), 593D (self 4) and 462D-7 (self 4) crossed with derivatives of Mo17, including 572D (backcross 1, self 2), 577D (backcross 1, self 2) and 585D (backcross 1, self 2). The derivative hybrids were not dwarf height at that stage of the breeding program. The trial experienced 47 days of a heat wave with light ineffectual showers of rain. Table 5 shows the results of the trial; column 1 shows the pedigree, column 2 shows the average yield in t/Ha, column 3 shows the percent of hybrids having 3 ears, column 4 shows the percent of hybrids having 2 ears, column 5 shows the percent of hybrids having 1 ear, column 6 shows the percent of hybrids having 0 ears and column 7 shows the average height in centimeters.

TABLE 5

| Pedigree | Ave Yield (t/Ha) | 3 ears (%) | 2 ears (%) | 1 ear (%) | 0 ears (%) | Height (cm) |
|---|---|---|---|---|---|---|
| 591D × 577D | 6.594 | 23.6 | 61.8 | 14.6 | 0 | 170 |
| 462D-9 × 572D | 6.506 | 2 | 77.6 | 18.4 | 2 | 160 |
| 593D × 572D | 5.679 | 0 | 84.3 | 13.7 | 2 | 150 |
| 460D × 585D | 5.207 | 2 | 41 | 13 | 0 | 160 |
| 462D-7 × 572D | 5.138 | 0 | 69.6 | 17.4 | 0 | 140 |
| Mo17 × A554N | 3.358 | 13 | 37.2 | 60.8 | 2 | 180 |

As shown in Table 5, the derivative hybrids of the present invention had greater yield and produced a greater number of plants having 2 or more ears than the hybrid A554N× Mo17$^8$.Ht,HtN, thus unexpectedly, the addition of short internodes and protogyny increased the yield of the hybrids. For maize plants to express their prolificacy fully they should not be planted at more than 40,000 plants per hectare.

Example 6. Comparison of Maize Hybrids Derived from B73$^6$.Ht,HtN, A228N and Mo17$^8$.Ht,HtN A yield trial was planted in which test crosses of derivatives of the three parent lines to which short internodes and protogyny had been added were compared with a commercial hybrid. The population density was 38,500 plants per hectare, which is low. For prolific maize to express prolificacy fully preferably they should be planted at less than 40,000 plants per hectare. The derivatives of the present invention used in the comparison were derivatives of inbred B73$^6$.Ht.HtN, including 513D (self 6) and 970C-14-7-8-11 (self 6), derivatives of inbred A228N, including 538D-6 (self 8), 285D (self 6), 344D-7-2 (self 8), 547D-2 (self 7), 344D-7-4 (self 7) and 500D-3 (self 7), and derivatives of Mo17, including 437D (backcross 1, self 1), 585D (backcross 1, self 2), 577D (backcross 1, self 2), 555D (backcross 1, self 2), 590D (backcross 1, self 2) and 572D (backcross 1, self 2). The commercial control was a variety grown by farmers in the area. The trial experienced 47 days of a heat wave with light ineffectual showers of rain. Table 6 shows the results of the trial; column 1 shows the pedigree, column 2 shows the average yield in tonnes/Hectare (t/Ha), column 3 shows the percent of hybrids having 5 ears, column 4 shows the percent of hybrids having 4 ears, column 5 shows the percent of hybrids having 3 ears, column 6 shows the percent of hybrids having 2 ears, column 7 shows the percent of hybrids having 1 ear and column 8 shows the average height in centimeters.

TABLE 6

| Pedigree | Ave Yield (t/Ha) | 5 ears (%) | 4 ears (%) | 3 ears (%) | 2 ears (%) | 1 ear (%) | Height (cm) |
|---|---|---|---|---|---|---|---|
| 513D × 437D | 7.928 | | | | 60 | 40 | 144 |
| 547D-2 × 555D | 7.651 | | 7 | 80.3 | 12.7 | | 209 |
| Control | 7.045 | | | 34.7 | 65.3 | | 229 |
| 344D-7-2 × 577D | 6.813 | | 1.3 | 31.1 | 60.8 | 6.8 | 170 |
| 344D-7-4 × 590D | 6.319 | | | 10.7 | 65.3 | 24 | 146 |
| 970C-14-7-8-11 × Mo17 | 6.204 | | | | 1.4 | 98.6 | 177 |
| 500D-3 × 572D | 6.054 | 1.3 | | 49.3 | 38.7 | 8 | 142 |
| 285D × 437D | 5.814 | | 2.7 | 23 | 66.2 | 10.8 | 156 |
| 538D-6 × 585D | 5.542 | | | 1.3 | 56 | 42.7 | 159 |
| 285D × 437D | 5.402 | | 2.8 | 18.6 | 65.7 | 12.9 | 144 |

As shown in Table 6, the derivative hybrids were shorter and had a greater percentage of plants having 2 or more ears when compared to the control.

Example 7. Yield Comparison of Test Crosses

In the 2011/2012 season the planting of yield trials was delayed until half-way through the summer in South Africa to December because of drought. In one trial three replications were planted, each one at a different population density. One plot had a population density of 158,000 plants per hectare, which is almost double the plant density at which maize is planted in the U.S., and this plot yielded 9.547 tonnes per hectare. The highest yielding test plot yielded 11.044 tonnes per hectare at a population density of 150,000 plants per hectare, despite being planted half-way through the summer and being subjected to drought. The altitude of the yield trial was 1720 meters, which placed a limitation on the number of available heat units. The dry year provided an excellent test for the test crosses. The height of the test crosses was about 1.2 meters. Where ears were damaged by birds, the average weight of the undamaged ears was multiplied by the total number of ears to obtain an estimate of the yield. The plants used for the test cross included EF70*13N, 9M, 8M, EF70*8N and EF70*14N. The EF70 lines are all derivatives of Mo17 that give dwarf hybrids when crossed with APN318. 8M and 9M are lines selected out of APN318. Table 7 shows the results of the test crosses; column 1 shows the pedigree, column 2 shows the number of plants, column 3 shows the number of lodged plants, column 4 shows the average number of ears per plant, column 5 shows the average number of ears damaged, column 6 shows the grain weight in kg of undamaged ears, column 7 shows the grain weight average per ear in kg, column 8 shows the grain weight in kg calculated due to damage, column 9 shows the percent moisture, column 10 shows the grain weight in kg at 13% moisture, column 11 shows the yield in tonnes/Hectare (t/Ha) and column 12 shows the planting density per hectare.

TABLE 7

| Pedigree | No. plants | Lodged plants | No. ears | Damaged ears | Grain Wt undamaged (kg) | Grain Wt Average per ear (kg) | Grain Wt calculated (kg) | Moisture (%) | Grain Wt at 13% (kg) | Yield (t/Ha) | Plants per Hectare |
|---|---|---|---|---|---|---|---|---|---|---|---|
| EF70*13N × 9M | 18 | 0 | 19 | | | 0.05 | 0.95 | 14.6 | 0.933 | 8.638 | 150,000 |
| 8M × EF70*8N | 18 | 0 | | | 0.76 | | 0.76 | 13.5 | 0.756 | 7 | 150,000 |
| EF70*14N × 8M | 19 | 3 | 21 | 0 | 1.04 | 0.05 | 1.04 | 13.5 | 1.034 | 9.574 | 150,333 |
| 8M × EF70*8N | 18 | 2 | 17 | 7 | 0.7 | 0.07 | 1.19 | 12.3 | 1.193 | 11.044 | 150,000 |

As shown in Table 7, the test crosses gave high yields despite being planted half-way through the summer and the heat units being limited by the altitude of 1720 meters.

The branches at the end of which the ears of maize develop (the shanks) generally have very short internodes. When the ears are covered to prevent fertilization, ears tend to develop on the nodes of the shank below the main ear. Ears do not develop on the nodes of the long internodes of the main stem above and below where the shank is attached. Presumably when the main ear is not fertilized, and the kernels do not develop on the ear, there is a build up of photosynthate which would normally be taken up by the developing ear. Such an increase in the supply of photosynthate in the short internode shank stimulates the buds at the nodes of these short internodes to start developing to form secondary ears. Generally the internodes at the base of the maize stalk are very short. At the end of the season when the grain is fully developed and is no longer utilizing photosynthate, sweet tasting juice tends to gather in the base of the maize stalk. Under these conditions ears tend to develop at the nodes of these short internodes at the base of the maize stalk.

Based upon these observations it appears that at higher concentrations of photosynthate the buds at the nodes of maize are stimulated to develop into ears. This is particularly the case, but not exclusively so, at the nodes of short internodes. The nodes at short internodes seem to be preferentially stimulated to develop ears because the threshold at which ear development is initiated is lower at the nodes of short internodes.

When maize plants are subjected to moisture stress when they come into flower, the ears tend not to exert silks. The effect of moisture stress on the plants is that photosynthesis stops. When the plant receives moisture again, photosynthesis recommences and the ears exert their silks. The silks grow very rapidly and require a sufficient level of photosynthate supply to do so. In the case of wild type maize, the silks are exerted three days after the commencement of pollen shed. This is probably because the level of photosynthate required for silk exertion is only attained three days after pollen shed commences. In the case of protogynous maize, it would not be possible for the silks to be exerted earlier than pollen shed commences if sufficient photosynthate is not available at that stage. This implies a higher level of photosynthetic activity by the plant. In other words, the plant has to be photosynthetically more efficient in order for it to be protogynous. The degree of photosynthetic efficiency of the plant will determine the level of photosynthate supply at the various stages of development of the plant. The higher the degree of efficiency of photosynthesis, the greater the level of photosynthate, and the greater the number of ears that are stimulated to develop and produce grain. The degree of earliness of silk exertion in relation to the commencement of pollen shed is therefore an indicator of the photosynthetic efficiency and the productive capacity of the plant.

Further Embodiments of the Invention

The goal of plant breeding is to combine in a single variety of hybrid, various desirable traits. For field crops, these traits may include resistance to diseases and insects, tolerance to heat and drought, reducing the time to crop maturity, greater yield, and better agronomic quality. With mechanical harvesting of many crops, uniformity of plant characteristics, such as germination and stand establishment, growth rate, maturity, and plant and fruit height, is important.

Field crops are bred through techniques that take advantage of the plant's method of pollination. A plant is self pollinated if pollen from one flower is transferred to the same or another flower of the same plant. A plant is cross-pollinated if the pollen comes from a flower on a different plant.

Plants that have been self-pollinated and selected for type for many generations become homozygous at almost all gene loci and produce a uniform population of true breeding progeny. A cross between two homozygous lines produces a uniform population of hybrid plants that may be heterozygous at a number of gene loci. A cross of two plants each heterozygous at a number of gene loci will produce a population of hybrid plants that differ genetically and will not be uniform.

Maize plants can be bred by both self-pollination and cross-pollination techniques. Maize has separate male and female flowers on the same plant located on the tassel and the ear respectively. Natural pollination occurs when wind blows pollen from the tassels to the silks that protrude from the tops of incipient ears. During silking, each potential kernel (ie ovule) on an ear produces a tube-like structure called a silk. The silk grows until it emerges from the husks surrounding the ear tip. Pollination occurs when silks protruding from the earshoots intercept pollen grains. Intercepted pollen grains germinate on the silk, each sending out a tube that grows down the centre of each silk towards the ovule. When the tube finally enters the embryo sac, it ruptures releasing two sperm, which fuse with the egg to initiate development of both the embryo and kernel. In order for a given ear to have a full compliment of grain, each ovule must be fertilised. In order for each ovule to be fertilised, viable pollen must be present during or shortly after the emergence of the silks. In current maize germplasm and morphologies, silk emergence normally occurs after the maize plant begins to shed pollen. If stress reaches a certain magnitude, such as that produced by drought or increased population density, then silking is further delayed.

The development of maize hybrids requires the development of homozygous inbred lines, the crossing of these lines, and the evaluation of crosses. Pedigree breeding and recurrent selection methods are used to develop inbred lines from breeding populations. Breeding programmes combine the genetic backgrounds from two or more inbred lines or various other broadbased sources into breeding pools from which new inbred lines are developed by selfing and selection of desired phenotypes. The new inbreds are crossed with other inbred lines and the hybrids from these crosses are evaluated to determine which of those have commercial potential.

Pedigree breeding starts with the crossing of two genotypes, each of which may have one or more desirable characteristics that is lacking in the other or which complement the other. If the two original parents do not provide all of the desired characteristics, other sources can be included in the breeding population. In the pedigree method, superior plants are selfed and selected in successive generations. In the succeeding generations the heterozygous condition gives way to homozygous lines as a result of self-pollination and selection. Typically in the pedigree method of breeding five or more generations of selfing and selection is practised: F1→F2; F2→F3; F3→F4; F4→F5; etc.

Backcrossing can be used to improve an inbred line. Backcrossing transfers a specific desirable trait from one inbred or source to an inbred lacking that trait. This can be accomplished for example by first crossing a superior inbred (A) (recurrent parent) to a donor inbred (non-recurrent parent), which carries the appropriate gene (s) the trait in question. The progeny of this cross is then mated back to the superior recurrent parent (A) followed by selection in the resultant progeny for that desired trait to be transferred from the non-recurrent parent. After five or more backcross generations with selection for the desired trait, the progeny will be heterozygous for loci controlling the characteristics being transferred, but will be like the superior parent for most or almost all other genes. The last backcross generation would be selfed to give pure breeding progeny of the gene (s) transferred.

A single cross maize variety is the cross of two inbred lines, each of which has a genotype which complements the genotype of the other. The hybrid progeny of the first generation is designated F1. In the development of hybrids only the F1 hybrid plants are sought. Preferred F1 hybrids are more vigorous than their inbred parents. This hybrid vigor, or heterosis, can be manifested in many polygenic traits, including increased vegitative growth and increased yield.

The development of hybrid maize involves three steps: (1) the selection of plants from various germplasm pools; (2) the selfing of the selected plants for several generations to produce a series of inbred lines, which, although different from each other, breed true and are highly uniform; and (3) the crossing of selected inbred lines with unrelated inbred lines to produce the hybrid progeny (F1). An important consequence of the homozygosity and homogeneity of the inbred lines is that the hybrid between any two inbreds will always be the same. Once the inbreds that give a superior hybrid have been identified, the hybrid seed can be reproduced indefinitely as long as the homogeneity of the inbred lines is maintained.

A single cross hybrid is produced when two inbred lines are crossed to produce the F1 progeny. A double cross hybrid is produced from four inbred lines crossed in pairs (A×B and C×D) and then the two F1 hybrids are crossed again (A×B and C×D). Much of the hybrid vigor exhibited by the F1 hybrids is lost in the next generation (F2). Consequently, seed from hybrid varieties is not used for planting stock.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. For example, if the range 10-15 is disclosed, then 11, 12, 13, and 14 are also disclosed. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

DEPOSIT INFORMATION

Deposits of the proprietary maize seed APN305 and APN318 of the present invention INCREASING THE NUMBER OF GRAIN BEARING EARS OF MAIZE disclosed above and recited in the appended claims have been made with the National Collections of Industrial, Food and Marine Bacteria (NCIMB), 23 St Machar Drive, Aberdeen, Scotland, AB24 3RY, United Kingdom. The date of deposits was May 21, 2012. The deposits of 2,500 seeds were taken from the same deposits maintained by the inventor in Harrismith, South Africa since prior to the filing date of this application. All restrictions will be irrevocably removed upon granting of a patent, and the deposits are intended to meet all of the requirements of 37 C.F.R. §§1.801-1.809. The NCIMB Numbers are 41974 and 41975, respectively. The deposits will be maintained in the depository for a period of thirty years, or five years after the last request, or for the enforceable life of the patent, whichever is longer, and will be replaced as necessary during that period.

While a number of exemplary aspects and embodiments have been discussed above, those of skill in the art will recognize certain modifications, permutations, additions and sub-combinations thereof. It is therefore intended that the following appended claims and claims hereafter introduced are interpreted to include all such modifications, permutations, additions, and sub-combinations as are within their true spirit and scope.

What is claimed is:

1. A method of producing prolific, protogynous dwarf maize plants, the method comprising:
   a) planting and growing a population of heterozygous maize plants selected from the group consisting of landraces and open pollinated varieties;
   b) selecting polygenic dwarf plants from said population to produce selected plants and inbreeding said selected plants to produce selected inbred plants;
   c) planting and growing one or more prolific inbred maize plants and said selected inbred plants;
   d) crossing said selected inbred plants with the prolific inbred maize plants to produce F1 hybrid plants;
   e) self-pollinating said F1 hybrid plants to produce a segregating F2 generation;
   f) selecting prolific dwarf plants having at least two ear shoots from said segregating F2 generation;
   g) self-pollinating the lowest ear of said selected prolific dwarf plants;
   h) harvesting and growing seed from said lowest ear of selected prolific dwarf plants to produce selected self-pollinated prolific dwarf maize plants having at least two or more grain bearing ears; and
   i) selecting protogynous plants from said selected self-pollinated prolific dwarf maize plants having at least two or more grain bearing ears.

2. The method of claim 1 further comprising:
   j) self-pollinating and growing selected protogynous plants until one or more prolific, protogynous dwarf maize plants are produced having at least two or more grain bearing ears;
   k) planting and growing seed of different inbred maize plants and of said prolific, protogynous dwarf maize plants produced in step j);
   l) bulking the pollen of the prolific, protogynous dwarf maize plants grown in step k) to produce bulked pollen;
   m) pollinating the different maize plants grown in step k) with said bulked pollen to produce an F1 population;
   n) selecting vigorous plants from said F1 population;
   o) bulking the pollen of the selected vigorous plants to produce bulked pollen of the selected vigorous plants;
   p) pollinating the selected vigorous plants with said bulked pollen of the selected vigorous plants;

q) selecting protogynous, dwarf plants having at least two or more grain bearing ears and shortened internodes between the two top grain-bearing ears;
r) self-pollinating said selected plants of step g) to produce seed of selfpollinated selected plants;
s) growing seed of said self-pollinated selected plants of step r);
t) repeating steps q) through s) until one or more inbred, protogynous, prolific dwarf plants are produced having at least two or more grain bearing ears and internodes between the ears of about 70 mm or less.

3. The method of claim 1, wherein said prolific inbred maize plants of step c) are inbred line B254W.

4. The method of claim 1, wherein the selected prolific dwarf plants in step f) have shortened internodes.

5. The method of claim 2, wherein the different maize plants grown in step k) are selected from the group comprising inbred lines A228N, B73$^6$.Ht.HtN and A554N.

6. The method of claim 2, wherein said vigorous plants have well-developed tillers.

\* \* \* \* \*